United States Patent [19]
Ho

[11] Patent Number: 5,807,814
[45] Date of Patent: Sep. 15, 1998

[54] BIS(THIO)ETHYLENE ASHLESS WEAR INHIBITORS AND LUBRICATING OILS AND GREASES

[75] Inventor: Andrew W. Ho, Pinole, Calif.

[73] Assignee: Chevron Chemical Company, San Ramon, Calif.

[21] Appl. No.: 676,048

[22] Filed: Jul. 5, 1996

[51] Int. Cl.$^6$ ................................. C10M 135/22
[52] U.S. Cl. .................... 508/447; 508/448; 508/570; 508/571; 558/186; 560/152; 564/204; 568/29; 568/38; 568/42
[58] Field of Search ................... 508/447, 448; 558/186; 560/152; 564/204

[56] References Cited

U.S. PATENT DOCUMENTS

| | | | |
|---|---|---|---|
| 2,533,233 | 12/1950 | Edwards et al. | 260/465.8 |
| 2,653,910 | 9/1953 | Airs et al. | 252/45 |
| 2,766,247 | 10/1956 | Middleton | 260/286 |
| 2,883,368 | 4/1959 | Middleton | 508/448 |
| 2,995,569 | 8/1961 | Hamilton et al. | 260/327 |
| 3,260,709 | 7/1966 | Nield | 508/448 |
| 3,673,090 | 6/1972 | Waldbillig et al. | 252/45 |
| 3,723,316 | 3/1973 | Mossie | 508/448 |
| 3,761,596 | 9/1973 | Taninaka et al. | 424/277 |
| 3,876,550 | 4/1975 | Holubec | 252/47.5 |
| 4,007,279 | 2/1977 | Ohtsuka et al. | 424/277 |
| 4,042,514 | 8/1977 | Giolito et al. | 252/48.6 |
| 4,058,469 | 11/1977 | Hoke | 508/448 |
| 4,070,295 | 1/1978 | Miller | 508/447 |
| 4,119,549 | 10/1978 | Davis | 252/45 |
| 4,125,479 | 11/1978 | Chesluk et al. | 252/33.6 |
| 4,147,640 | 4/1979 | Jayne et al. | 252/45 |
| 4,148,737 | 4/1979 | Liston et al. | 252/32.7 E |
| 4,191,659 | 3/1980 | Davis | 252/45 |
| 4,209,408 | 6/1980 | Hoke | 508/447 |
| 4,389,400 | 6/1983 | Ho | 424/248.52 |
| 4,427,667 | 1/1984 | Ho | 424/210 |
| 4,447,450 | 5/1984 | Ho | 424/304 |
| 4,648,985 | 3/1987 | Thorsell et al. | 252/32.5 |
| 4,859,352 | 8/1989 | Waynick | 252/41 |
| 4,879,054 | 11/1989 | Waynick | 252/41 |
| 4,880,551 | 11/1989 | Doe | 252/47.5 |

*Primary Examiner*—Ellen M. McAvoy
*Attorney, Agent, or Firm*—Ernest A. Schaal

[57] ABSTRACT

Oil soluble compounds having the formula:

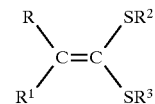

wherein R and $R^1$ are independently cyano, alkoxycarbonyl, aryloxycarbonyl, alkenyloxycarbonyl, alkylcarbonyl, arylcarbonyl, alkenylcarbonyl, alkylsulfonyl, arylsulfonyl, alkenylsulfonyl, substituted aminocarbonyl, alkylphosphoryl, arylphosphoryl, alkenylphosphoryl, aryl, or heterocyclics, or together form a carbocycle or heterocycle, and $R^2$ and $R^3$ are independently alkyl, alkenyl, hydroxyalkyl, sulfurized alkyl, alkoxycarbonylalkyl, arylalkyl, or borated hydroxyalkyl, with the proviso that R, $R^1$, $R^2$ and $R^3$ together contain sufficient carbon atoms to render the compound oil soluble in an oil of lubricating viscosity. The compound are useful as wear protectants or extreme pressure agents to enhance wear protection or extreme pressure properties in lubricating oils and greases.

15 Claims, No Drawings

BIS(THIO)ETHYLENE ASHLESS WEAR INHIBITORS AND LUBRICATING OILS AND GREASES

BACKGROUND OF THE INVENTION

This invention relates to certain 2,2-dithiolethylene derivatives and the manufacture thereof. In a further aspect, the invention relates to the use of such derivatives as antiwear or extreme pressure additives in lubricating compositions to prevent or reduce wear and corrosion between sliding or contacting moving parts and to lubricating compositions and hydraulic or functional fluids containing such additives.

Antiwear agents and extreme pressure agents are used to provide wear protection in a variety of lubricating compositions including internal combustion engine oils, gear oils, transmission fluids, industrial oils, cutting oils, greases and the like. Engine oils that provide wear protection are very important for automobile spark ignition and diesel engines because such engines have valve train systems, including valves, cams, and rocker arms, which present special lubrication concerns. It is extremely important that the lubricant, i.e., the engine oil, protects these parts from wear. Engine oils use a mineral oil or a synthetic oil as a base oil. However, simple base oils alone do not provide the necessary properties to provide the necessary wear protection, deposit control, etc., required to protect internal combustion engines. Thus, base oils are formulated with various additives for imparting auxiliary functions, such as ashless dispersants, metallic detergents (i.e., metal-containing detergents), antiwear agents, antioxidants (i.e., oxidation inhibitors), viscosity index improvers, and the like to give a compounded oil (i.e., a lubricating oil composition).

A number of such engine oil antiwear additives are known and employed in practice. Zinc dialkyldithiophosphates are contained in most of the commercially available internal combustion engine oils, especially those used for automobiles, because of their favorable characteristics as an antiwear agent and performance as an oxidation inhibitor.

However, a problem has arisen with respect to the use of zinc dialkyldithiophosphate, because phosphorous derivatives poison catalyst components of catalytic converters. This is a major concern, because effective catalytic converters are needed to reduce pollution and to meet governmental regulation designed to reduce toxic gases, such as hydrocarbons, carbon monoxide, and nitrogen oxides, in internal combustion engine exhaust emission. Such catalytic converters generally use a combination of catalytic metals, such as platinum or variations, and metal oxides. They are installed in the exhaust streams, e.g., the exhaust pipes of automobiles, to convert the toxic gases to nontoxic gases. As before mentioned, these catalyst components are poisoned by the phosphorous component, or the phosphorous decomposition products of the zinc dialkyldithiophosphate. Accordingly, the use of engine oils containing phosphorous additives may substantially reduce the life and effectiveness of catalytic converters. Therefore, it would be desirable to reduce the phosphorous content in the engine oils so as to maintain the activity and extend the life of the catalytic converter. However, simply decreasing the amount of zinc dialkyldithiophosphate presents problems because this necessarily lowers the antiwear properties and oxidation inhibition properties of the lubricating oil. Therefore, it is necessary to find a way to reduce phosphorous content while still retaining the antiwear and oxidation or corrosion inhibiting properties of the higher phosphorous content engine oils.

In order to compensate for lowering the amount of zinc dialkyldithiophosphate, the use of other oxidation inhibitors such as phenol derivatives and amine derivatives have been studied. However, at best, the use of such known oxidation inhibitors in place of zinc dialkyldithiophosphate only marginally satisfies the required levels of antiwear and oxidation inhibition. The use of magnesium sulfonate detergents, which are also effective to enhance the antiwear properties in valve train systems, has also been studied and, in fact, some commercially available engine oils use a magnesium sulfonate detergent. However, engine oils containing a magnesium sulfonate detergent have drawbacks in that crystalline precipitates are sometimes produced when these engine oils are stored under humid or variable temperature conditions for a long period of time. Such precipitates may cause plugging of the filter, which is installed in the engine oil circulating system. Such plugging is more likely to occur when a large amount of the magnesium sulfonate detergent is used. Thus, the use of magnesium sulfonate detergents is not a satisfactory solution.

At the present time, demand for further decrease of phosphorous content is very high from the viewpoint of the aforementioned problems. For instance, it is sometimes desired to decrease the phosphorous content to levels below the regulated upper limit and the 0.1 wt. % phosphorous level of today's better engine oil. This reduction cannot be satisfied by the present measures in practice and still meet the severe antiwear and corrosion inhibiting properties required of today's engine oils.

Thus, it would be desirable to develop lubricating oils, and additives and additive packages therefore, having low levels of phosphorous but which still provide the needed wear protection and corrosion protection now provided by lubricating oils having higher levels of zinc dialkyldithiophosphate, but which do not suffer from the disadvantages of the low phosphorous level lubricants discussed above. There is also a continuing need for antiwear and extreme pressure additives in oil-based lubricating compositions generally including transmission fluids, heavy machinery gear oils, hydraulic tractor fluids, industrial fluids, cutting oils and greases.

U.S. Pat. No. 4,042,514 discloses certain 5-alkylthio and 5-alkylarylthio-1,2-thiole-3-thiones and 3-ones and the use of such compounds as extreme pressure and antioxidant additives for lubricating compositions. Based on U.S. Pat. No. 4,042,514 (Col. 1, lines 10–15), U.S. Pat. Nos. 2,653, 910; 2,995,569, and 3,673,090 disclose certain alkyl-or aryldithiole-thiones obtained by the sulfurization of polyisobutene as extreme-pressure, antiwear oil antioxidant lubricating oil additives. Canadian Patent No. 1,228,847 describes the use of aliphatic olefins in combination with certain sulfurized olefins to provide wear protection in hydrorefined lubricating oils. U.S. Pat. Nos. 4,119,549; 4,147,640; 4,148,737; 4,191,659 describe the use of various sulfurized compounds including sulfurized olefins, carboxylic acid esters, esterolefins, etc., as antioxidants or antiwear or extreme pressure additives for lubricating oil. Although a number of sulfurized organic compounds have been proposed as wear additives and extreme pressure agents or antioxidants, one cannot predict that a given sulfur containing organic compound or class of compounds will have any of these properties or even if they possess one or more of these properties that they will be compatible with the other components of the lubricating composition or will not in fact themselves create additional problems, notably copper corrosion.

U.S. Pat. No. 3,876,550 (issued 1975) discloses lubricating compositions containing an alkylene bis (dithiocarbamate), as an antioxidant, and a substituted succinic acid as a rust inhibitor. The alkylene dithiocarbamate is represented in the patent by the formula $R^1R^2N—C(S)—S$-alkylene-$S—C(S)—NR^3R^4$.

The use of dithiocarbamates as extreme pressure antiwear additives is also taught by U.S. Pat. No. 4,859,352 and U.S. Pat. No. 4,648,985 teaches that the combination of dithiocarbamates with zinc dithiophosphate and copper salts of carboxylic acid provide lubricants with extreme pressure properties.

The use of methylene bis(dibutyldithiocarbamate) as an oxidation inhibitor in lubricating oils, in combination with other ingredients, is also disclosed in U.S. Pat. Nos. 4,125,479 (1978) and 4,880,551 (1989).

U.S. Pat. No. 4,879,054 (1989) is directed to cold temperature greases and teaches using dithiocarbamates such as Vanlube 7723, i.e., 4,4'-methylene bis(dithiocarbamate), in such greases to provide extreme pressure antiwear properties (Col. 6, lines 18–28). Examples 13–18 (Col. 14, lines 26–32) describe using Vanlube 7723 and triarylphosphate as replacements for lead naphthenate and zinc dithiophosphate.

My prior U.S. Pat. Nos. 4,389,400; 4,427,667 and 4,447,450 disclose certain halogenated dithioethylene derivatives, which are useful as agricultural fungicides.

SUMMARY OF THE INVENTION

I have now unexpectedly discovered certain analogues of the compounds described in my previous dithioethylene derivative patents, which are useful as antiwear and/or extreme pressure additives in lubricating oil compositions and further which can be effectively used to replace all or more preferably a portion of the zinc dithiophosphate compounds typically used in such compositions. As compared with the components described in my U.S. patents cited above, I have discovered that by eliminating the chloro substituents, generally necessary for fungicide activity in this class of compounds and indeed present in many antiwear additives, and increasing oil solubility by increasing the number of carbon atoms in the molecules, provides a new class of compounds which exhibit useful antiwear or extreme pressure properties in lubricating oils, functional fluids and greases without containing environmentally undesirable substituents, such as halogens and phosphorous.

Thus in one aspect the invention provides compounds of the formula:

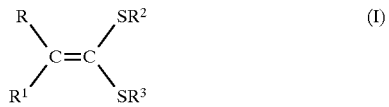

wherein R and $R^1$ are independently cyano, alkoxycarbonyl having four through thirty carbon atoms, aryloxycarbonyl having seven through thirty carbon atoms, alkenyloxycarbonyl having eight through thirty carbon atoms, alkylcarbonyl having four through thirty carbon atoms, arylcarbonyl having seven through thirty carbon atoms, alkenylcarbonyl having eight through thirty carbon atoms, alkylsulfonyl having four through thirty carbon atoms, arylsulfonyl having seven through thirty carbon atoms, alkenylsulfonyl having eight through thirty carbon atoms, substituted aminocarbonyl having one through thirty carbon atoms, alkylphosphoryl having four through thirty carbon atoms, arylphosphoryl having seven through thirty carbon atoms, alkenylphosphoryl having eight through thirty carbon atoms, aryl having one through thirty carbon atoms, or heterocyclics; or R and R' together with the carbon atom to which they are joined form a saturated or unsaturated carbocycle having five or six carbon atoms optionally substituted with one or two alkyl groups independently having one through thirty carbon atoms, or a saturated or unsaturated heterocycle having five or six carbon atoms optionally substituted with one or two alkyl groups independently having one through thirty carbon atoms, and $R^2$ and $R^3$ are independently alkyl having seven through thirty carbon atoms, hydroxyalkyl having two through twenty carbon atoms, alkenyl having three through thirty carbon atoms, sulfurized alkyl having three through thirty carbon atoms and one or two sulfur atoms, alkoxycarbonylalkyl wherein the alkoxy moiety has two through five carbon atoms and the alkyl moiety has one through ten carbon atoms; arylalkyl having seven through thirty carbon atoms, or borated hydroxyalkyl having three through thirty carbon atoms, with the proviso that R, $R^1$, $R^2$ and $R^3$ together contain sufficient carbon atoms to render the compound oil soluble in an oil of lubricating viscosity.

Preferably, R and $R^1$ are independently cyano, alkoxycarbonyl having four through thirty carbon atoms, or R and $R^1$ together with the carbon atoms to which they are joined form a saturated or unsaturated carbocycle having five or six ring atoms optionally substituted with one or two alkyl groups independently having one through thirty carbon atoms.

As noted above, oil solubility is generally provided by the total number of carbon atoms in the R, $R^1$, $R^2$ and $R^3$ substituents. Thus, where one or more of these substituents is a small substituent, for example, where R and/or $R^1$ is cyano, oil solubility is provided by increasing the chain length or number of carbon atoms of the other substituents. Preferably, the sum of the carbon atoms in R, $R^1$, $R^2$ and $R^3$ is at least sixteen and more preferably is at least twenty.

In another aspect, the invention provides a lubricating oil composition comprising a major amount of an oil of lubricating viscosity and an amount of a compound of formula 1, or oil soluble salts thereof or mixtures thereof, which is effective to provide antiwear or extreme pressure protection.

In still another aspect, the invention provides a lubricating grease comprising an oil of lubricating viscosity, an amount of a compound, or mixture of compounds, of the invention effective to provide antiwear or extreme pressure protection and a sufficient amount of a compatible thickening agent to provide the desired grease consistency.

In a further aspect, the invention provides a concentrate composition comprising about from 0.5 to 30 wt. % of a compound or mixture of compounds of the invention and an inert hydrocarbon liquid diluent.

In a still further aspect, the invention provides a method for reducing wear between contacting moving or sliding metal parts which comprises lubricating such parts with the lubricating oil compositions or greases of the present invention.

Additional aspects of the invention will be apparent from the following description.

DETAILED DESCRIPTION OF THE INVENTION

The present invention is concerned with a novel genus of compounds which functions as antiwear agents and extreme pressure agents in various oil based lubricating compositions. A distinction is sometimes made between antiwear agents and extreme pressure agents. The former being considered to provide wear protection under normal conditions and may function as a surface pacifying agent or lubricity agent. The latter is considered to provide antiwear protection under more extreme conditions under which antiwear agents may be ineffective, and is theorized as reacting with the surface of the bearing parts to provide a protective or lubricating film. The compounds of the present invention enhance wear protection in lubricating oil compositions under both normal and extreme pressure conditions regardless of the particular mechanism that may be involved.

The preferred compounds of the invention in terms of performance are the compounds of Formula I wherein R and $R^1$ are independently cyano or alkoxycarbonyl having eight to thirty carbon atoms. Preferably the R substituent is identical to the $R^1$ substituent, more preferably both R and $R^1$ are alkoxycarbonyl, most preferably both R and $R^1$ are carbo-2-ethylhexoxy. Typically, best results are obtained in terms of performance, combined with ease of manufacture, where the compounds are identically substituted with $R^2$ and $R^3$. Preferably, both $R^2$ and $R^3$ are arylalkyl having seven through thirty carbon atoms.

DEFINITIONS

As used herein the following terms have the following meanings unless expressly stated to the contrary:

The term "alkyl" refers to both straight- and branched chain alkyl groups and includes primary, secondary and tertiary alkyl groups.

The term "alkenyl" refers to an alkyl group with unsaturation.

The term "aryl" refers to a substituted phenyl group.

The term "alkylcarbonyl" refers to the group

wherein R' is alkyl.

The term "alkenylcarbonyl" refers to the group

wherein R' is alkylene.

The term "arylcarbonyl" refers to the group

wherein R' is aryl.

The terms "alkoxycarbonyl" refer to the group

wherein R' is alkyl.

The terms "alkenyloxycarbonyl" refer to the group

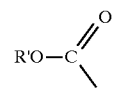

wherein R' is alkylene.

The terms "aryloxycarbonyl" refer to the group

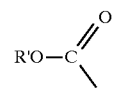

wherein R' is aryl.

The term "alkoxycarbonylalkyl" refers to the group

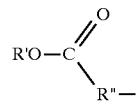

wherein R' is alkyl and R" is alkylene.

The term "alkylsulfonyl" refers to the group $RSO_2$ where R is alkyl.

The term "alkenylsulfonyl" refers to the group $RSO_2$ where R is alkenyl.

The term "arylsulfonyl" refers to the group $RSO_2$ where R is aryl.

The term "alkylphosphoryl" refers to the group $RPO(OR)_3$ where R is alkyl.

The term "alkenylphosphoryl" refers to the group $RPO(OR)_3$ where R is alkenyl.

The term "arylphosphoryl" refers to the group $RPO(OR)_3$ where R is aryl.

The term "arylalkyl" refers to an alkyl group substituted with an aryl group.

The term "hydroxyalkyl" refers to an alkyl group substituted with an hydroxyl group.

The term "borated hydroxyalkyl" refers to the reaction product of a hydroxyalkyl with boric acid.

The term "carbocycle" refers to a saturated cyclic group with a carbon skeleton.

The term "cyano" refers to the—CN group.

The term "heterocyclics" refers to a saturated or unsaturated saturated cyclic group with a carbon skeleton wherein the skeleton is substituted with at least one hetero atom.

The term "substituted aminocarbonyl" refers to the group

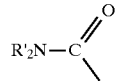

wherein R' is alkyl.

The term "sulfurized alkyl") refers to an alkyl group that has been substituted with sulfur.

The term "The term Total Base Number" or "TBN" refers to the amount of base equivalent to milligrams of KOH in 1 gram of sample. Thus, higher TBN numbers reflect more alkaline products and therefore a greater alkalinity reserve. The TBN of a sample can be determined by ASTM Test No. D2896 or any other equivalent procedure.

The term "oil solubility" means that the additive has a solubility of at least 50 grams per kilogram and preferably at least 100 grams per kilogram at 200° C. in a base 10W40 lubricating oil.

The term "oil of lubricating viscosity" generally refers to an oil having a viscosity of 3–20 cSt at 100° C. in the case of lubricating oil compositions and may be a single oil or a blend of oils. In the case of greases more viscous oils may also be used.

SYNTHESIS

In general the compounds of the present invention can be prepared by adapting the procedures described in my U.S. Pat. Nos. 4,389,400 and 4,447,450, hereby incorporated by reference in their entirety, by employing the appropriate starting materials corresponding to the substituent desired in the compounds of the present invention.

The compounds of Formula I wherein $R^2$ is identical to $R^3$ can be conveniently prepared by the reaction of the corresponding bis(2,2 thioate) metal salt with the corresponding halides:

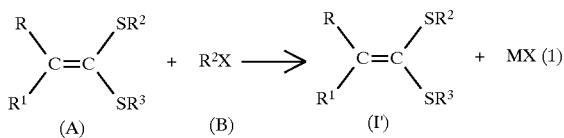

wherein R, $R^1$ and $R^2$ are as defined herementioned, X is halide, preferably chloride or bromide, and M is a metal cation, preferably an alkali metal, for example potassium or ammonium cation. (Also, although M is shown as a monovalent cation for the sake of simplicity, M could also be a divalent or polyvalent cation, in which case M would be represented as $M_{1/r}$ wherein r is the valence of M).

This process can be conveniently effected by contacting Compound (A) with Compound (B), under reactive conditions, preferably in an inert organic solvent.

Typically, the process is conducted at temperatures in the range of about from –10° C. to 50° C., preferably about from 20° to 40° C., for about from 1 to 48 hours, preferably about from 4 to 8 hours, using about from 2 to 4 moles, preferably 2 to 2.2 moles, of (B) per mole of Compound (A). Suitable inert organic solvents which can be used include, for example, dimethylformamide, toluene, methanol, and compatible mixtures thereof.

In general the compounds wherein $R^2$ and $R^3$ are the same are preferred because of the ease of preparing such compounds by the procedure described above. However, if desired, the compounds of formula I wherein $R^2$ and $R^3$ are different, or the same for that matter, can be prepared by the following process schematically represented by the following sequence of overall reaction equations:

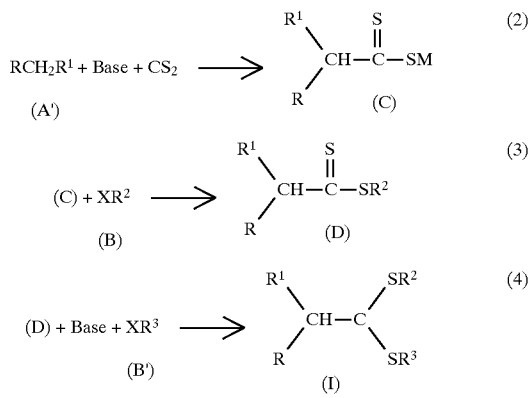

wherein R, $R^1$, $R^2$, $R^3$ and x are as defined hereinabove.

The first step in this process can be conveniently effected by contacting compound A' with an inorganic base (B') (e.g. potassium hydroxide) and carbon disulfide under reactive conditions, preferably in an inert organic solvent.

Typically, this process step (2) is conducted at temperatures in the range of about from 0° to 50° C., preferably 0° to 20 C., for about from ½ to 4 hours, preferably 1 to 2 hours, using about from 2 to 3 equivalents, preferably 2 to 2.1 equivalents, inorganic base and 1 to 2.5 equivalents of carbon disulfide per mole of Compound (A'). Suitable inert organic solvents which can be used include, for example, dioxane, tetrahydrofuran, dimethylformamide and the like and compatible mixtures thereof. Suitable inorganic bases include, for instance, potassium hydroxide, sodium carbonate, potassium carbonate, and the like. Preferably, the reaction employs pulverized potassium hydroxide as the base in a dimethylformamide medium.

The compounds of Formulas (A') are generally known compounds and can be prepared by known procedures or by obvious modifications thereof (e.g., by using appropriately substituted starting materials).

The next reaction step (3) can be conveniently effected by contacting compound (C) with the appropriate organic halide (B) having the desired $R^2$ substituent, under reactive condition, preferably in an inert organic solvent.

This step of this process is typically conducted at temperatures in the range of about from 0° to 100° C., preferably 20° to 80° C., for about from 1 to 26 hours, preferably 4 to 8 hours, using about from 1 to 2 moles, preferably 1 to 1.1 moles of compound (B) per mole of compound (C). Suitable inert organic solvents which can be used include, for example, those described with respect to reaction equation (1) used to make compounds (I'), and the like.

The last reaction step (4) can be effected by contacting compound (D) with inorganic base and compound (B') under reactive conditions, preferably in an inert organic solvent, and is conveniently conducted in situ with the reaction product mixture of the previous reaction step (3) without removal of the organic solvent. Process reaction step (4) is typically conducted at temperatures in the range of about from 0° to 100° C., preferably 20° to 80° C., for about from 1 to 26 hours, preferably 4 to 8 hours, using about from 1 to 2 equivalents preferably 1 to 1.1 equivalents, of inorganic base and 1 to 2 equivalents, preferably 1 to 1.2 equivalents, of compound (B') per compound (D). Suitable inert organic bases and inert organic solvents that can be used include those already described above with respect to the preceding reaction step.

The starting materials of formula A can be prepared by the same general procedure as reaction step (2) by increasing the amount of inorganic base to produce the bis salt instead of the mono-salt:

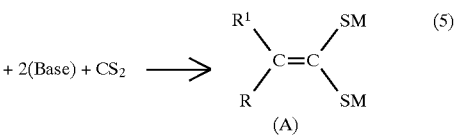

wherein R, $R^1$ and M are defined hereinabove.

Reaction step (5) can be conveniently conducted by adding 2 to 2.5 equivalents of an inorganic base to the appropriate reagent A'. The reaction is done in the liquid phase employing an inert organic solvent, such as dioxane, dichloromethane, tetrahydrofuran, diethyl ether, and the like. Suitable inorganic bases include, for instance, potassium hydroxide, sodium carbonate, potassium carbonate, and the like. Preferably, the reaction employs pulverized potassium hydroxide as the base in a dioxane medium. 1 to 2.5 equivalents of carbon disulfide is then added to the system. The reaction is generally conducted at from 0° to 100°C., although preferably at from 5° to 40° C., and is generally completed from within 1 to 24 hours. In some instances it may be convenient to conduct reaction step in situ with the reaction product mixture produced by step (5) without removal of the solvent.

Reaction steps (2), (4) and (5) involve the addition of a solid base to an inorganic solvent. In order to facilitate reaction completion, a phase-transfer catalyst is preferably employed in these reactions to aid in the transfer of the solid base into the organic solvent. Preferred catalysts include, for instance, tetraalkylammonium halides. A particularly preferred catalyst is tetra-n-butylammonium bromide. In general, 0.025 equivalents of the catalyst have been found sufficient to accomplish the catalytic effect desired. Alternatively, if the base employed is an aqueous solution, a phase-transfer catalyst is useful to facilitate transfer from the aqueous phase to the organic phase.

Reactions (3) and (4) involve adding a potassium thiolate to an organic medium. Preferably, in order to speed the time required for reaction, a catalytic amount (for example about 0.025 equivalents) of a phase-transfer catalyst is added. Catalysts such as tetraalkylammonium halide salts are generally preferred.

Suitable bases which can be used include for example, sodium hydroxide, potassium hydroxide, sodium ethoxide, sodium carbonate, potassium carbonate, alkali metal alkoxides, and the like. Suitable phase transfer agents are agents which transfer hydrophilic ions into a lipophilic organic medium and include, for example, benzyl triethylammonium chloride, tetra-n-butylammonium chloride, methyltrioctylammonium chloride, tetra alkylphosphonium halides, and the like.

The compounds of formula wherein $R^2$ and $R^3$ are sulfurized alkyl, can also be conveniently prepared by first preparing the desired $R^2$, $R^3$ olefin of formula I and reacting this compound with the desired amount of sulfur. Such sulfurization procedures are known to the art and generally involve contacting an olefin with powdered or liquid sulfur, or a sulfur equivalent, e.g. $SCL_2$, under reactive conditions at temperatures in the range of about from 80° to 110° C., typically in an inert organic solvent such as toluene.

GENERAL PROCESS CONDITIONS

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole or equivalent ratios of reactants, solvents, etc.) have been given, that other process conditions could also be used. Optimum reaction conditions (e.g., temperature, reaction time, mole ratios, solvents, etc.) may vary with the particular reagents or organic solvents used but can be determined by routine optimization procedures.

LUBRICATING COMPOSITIONS

The lubricating oil compositions of the present invention can be conveniently prepared by simply blending or mixing of the compound(s) of formula I and/or an oil soluble salt thereof with an oil of lubricating viscosity (base oil). The compounds of the invention may also be preblended as a concentrate or package with various other additives in the appropriate ratios to facilitate blending of a lubricating composition containing the desired concentration of additives. The compounds of the present invention are blended with base oil a concentration at which they provide wear protection and are both soluble in the oil and compatible with other additives in the desired finished lubricating oil. Compatibility in this instance generally means that the present compounds as well as being oil soluble in the applicable treat rate also do not cause other additives to precipitate under normal conditions. Suitable oil solubility/compatibility ranges for a given compound of lubricating oil formulation can be determined by those having ordinary skill in the art using routine solubility testing procedures. For example, precipitation from a formulated lubricating oil composition at ambient conditions (about 20°–25° C.) can be measured by either actual precipitation from the oil composition or the formulation of a "cloudy" solution which evidences formation of insoluble wax particles.

Typically the lubricating oil composition of the invention contains about from 0.2 to 3 wt. %, preferably about from 0.5 to 2 wt % based on the total weight of the composition, of a wear protectant selected from the lubricating oil soluble compounds of formula I and mixtures thereof. More preferably, the lubricating composition contains about from 0.9 to 1.5 wt. % of the said wear protectant. The present compounds are compatible with, and can be advantageously used with, zinc dithiophosphates to increase wear protection or more preferably to reduce the amount of zinc dithiosphosphate which would otherwise be requested to provide a given level of wear protection.

The lubricating oil, or base oil, used in the lubricating oil compositions of the present invention are generally tailored to the specific use e.g. engine oil, gear oil, industrial oil, cutting oil, etc. For example, where desired as an engine oil, the base oil typically will be a mineral oil or synthetic oil of viscosity suitable for use in the crankcase of an internal combustion engine such as gasoline engines and diesel engines which include marine engines. Crankcase lubricating oils ordinarily have a viscosity of about 1300 cSt 0° F. to 24 cSt at 210° F. (99° C.). the lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity such as didodecyl benzene can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used. Blends of various mineral oils, synthetic oils and minerals and synthetic oils may also be advantageous, for example to provide a given viscosity or viscosity range. In general the base oils or base oil mixtures for engine oil are preselected so that the final lubricating oil, containing the various additives, including the present wear protectant, has a viscosity at 100° C. of 4 to 22 centistokes, preferably 10 to 17 centistokes and more preferably 13 to 17 centistokes.

Typically the lubricating oil composition will contain a variety of compatible additives desired to impart various properties to the finished lubricating oil composition depending on the particular end use and base oils used. Such additives include neutral and basic detergents such as natural and overbased organic sulfonates and normal and overbased phenates and salicylates, dispersants, ashless dispersants such as various polyalkylsuccinimides or polyalkylsuccimic acid esters, rust inhibitors, foam inhibitors, pour point dispersants, antioxidants, including the so called viscosity index (VI) improvers, dispersant VI improvers and, as noted above, other corrosion or wear inhibitors. The lubricating greases of the present invention may also contain other additives, though generally the number of other additives will be less extensive than for example in a high performance automotive engine oil.

The present lubricating compositions also include greases containing the present oil such as the base oils described above as well as more viscous mineral, natural, or synthetic oils and a thickening agent to provide the desired consistency to the grease. The base oil is generally used in an amount sufficient to balance the total grease composition, after accounting for the desired quantity of the thickening agent, and other additive components including in the grease formulation. A wide variety of materials can be employed as thickening or gelling agents. These can include fatty acid metal salts or soaps, such as calcium, or lithium stearates or hydroxystearates, which are dispersed in the lubricating vehicle in grease-forming quantities in an amount sufficient to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt or dissolve when used at the required temperature within a particular environment; however, in all other respects, any material which is normally employed for thickening or gelling hydrocarbon fluids for forming greases can be used in the present invention.

The present invention also provides an additive package or concentrate which may be added to an oil of lubricating viscosity either as the sole additive or in combination with other additives. (Generally, the additive package will not contain a viscosity index improver because even where desired the viscosity index improver is generally added to the base oil by the lubricant formulator.) Thus, a preferred additive concentrate contains about from 0.5 to 30 wt. % more preferably 5 to 10 wt. % of the wear protectant of the present invention and sufficient basic material (typically overbased detergents) to provide the concentrate with a TBN of about from 60 to 180 preferably 60 to 120; and about 1 to 10 wt. % preferably 2 to 6 wt. % of a diluent oil or other compatible inert organic liquid diluent. With the general exception of the VI improver, the concentrate will frequently also contain various other additives considered desirable from the intended use and generally will contain about from 30 to 60 wt. % of an ashless dispersant and frequently will also contain neutral or slightly alkaline detergent in addition to the overbased detergent. The amount of overbased detergent needed to provide the requisite TBN will, of course, vary with the TBN of the overbased detergent but typically will be 20 to 80 wt. % of the concentrate. The concentrate may also be provided as an individual concentrate containing about from 85 to 95 wt. % of the present wear protectant and about 5 to 15 wt. % of an inert organic liquid diluent designed from formulation either into an additives package or directly into the base oil. Additive packages or concentrates may also be provided for greases, though generally such packages will contain little more than the compounds of the present invention and perhaps other antiwear or extreme pressure agents.

Included in the lubricating oil compositions of the present invention are engine oils such as diesel engine oils, as noted above, including those used in marine diesel engines, locomotives, power plants and high speed automotive diesel engines, gasoline burning engines and compressors; functional fluids including automotive fluids such as automatic transmission fluids, power steering fluids and power brake fluids; gear oils including such oils are automotive spiral-bevel and worm-gear axle oils which operate under extreme pressures, load and temperature conditions, hypoid gear oils operating under both high speed, low torque and low speed, high torque conditions and various other industrial oils and cutting oils.

The various additive materials or classes of materials described above are known materials and can be prepared by known procedures or obvious modifications thereof and frequently are readily available from commercial sources. A listing of various additives and their function is for example described in columns 9 and 10 of U.S. Pat. No. 4,119,549 and U.S. Pat. No. 5,397,486, hereby incorporated by reference.

PREPARATIONS AND EXAMPLES

A further understanding of the invention can be had in the following nonlimiting Preparations and Examples. Wherein unless expressly stated to the contrary, all temperatures and temperature ranges refer to the Centigrade system and the term "ambient" or "room temperature" refers to about 20° C.–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined 300 mHz, using trimethylsilene deutrated chloroform signals are assigned as singlets (s), broad singlets (bs), doublets (d), double doublets (dd), triplets (t), double triplets (dt), quartets (q), and multiplets (m), and ppm refers to part per million.

EXAMPLE 1

1,1-DI(2-BUTENYLTHIO)-2,2 BIS(CARBO-2-ETHYLHEXOXY)ETHYLENE

In this example 340 grams (3.75 moles) of crotyl chloride was added dropwise to a mixture of 860.7 grams (1.79 moles) of dipotassium 2,2-bis(carbo-2-ethylhexoxy) ethylene 1,1-dithiolate) in 180 ml dimethyl formamide at room temperature (about 20°–25° C.) under a nitrogen atmosphere. The reaction mixture was stirred vigorously for 60 hours and then evaporated to remove the dimethylformamide solvent. The residue was dissolved in hexane and washed several times with water. The hexane solvent was evaporated off and the remaining oil residue was dissolved in a small amount of hexane and then filtered through silica gel. The filtrate was evaporated to dryness affording 649.4 grams of a reddish-brown translucent oil. The structure of the title compound was confirmed by nuclear molecular resonance and infrared spectra analysis. NMR at 0.88 ppm (t, 12H), 1.15–1.45 ppm (m, 16H), 1.65 ppm (m, 2H), 1.70 ppm (d, 6H), 3.55–4.20 ppm (m, 8H), and 5.10–6.10 ppm (m, 4H).

Similarly by applying the same procedure using the appropriate dithiolate salts and chloride reactants the following compounds can be respectively prepared:

1,1-di(2-pentenylthio)-2,2,-bis(carbo-2-ethylhexoxy)-ethylene; 1,1-di(2-hexenylthio)-2,2-bis(carbo-2-ethylhexoxy)ethylene; 1,1-dibenzylthio-2,2-bis(carbo-2-ethylhexoxy)ethylene; 1,1-di(4-nitrobenzylthio)-2,2-bis(carbo-2-ethylhexoxy)ethylene; 1,1-di(4-methoxybenzylthio)-2,2-bis(carbo-2-ethylhexoxy)ethylene; and 1,1-di(4-tolylthio)-2,2-bis(carbo-2-ethylhexoxy)ethylene.

EXAMPLE 2
1,1-DICYANO-2,2-BIS(DODECYLTHIO)ETHYLENE

In this example of 531.1 grams (2.13 moles) of 1 bromodedecane was added dropwise to a suspension of 232.5 grams 3,3-bis(potassium thiolate) of acrylodinitrile in 1000 ml of dimethylformamide at 100° C. under a nitrogen atmosphere. The reaction mixtures were stirred vigorously at this temperature for 48 hours and then cooled, and diluted with water and extracted with methyl chloride. The methyl chloride extract was washed several times with water and then with a saturated aqueous solution of sodium chloride. The washed extract was then dried with anhydrogous magnesium sulfate, filtered and then evaporated to remove the methyl chloride solvent. The residue was dissolved in a 50 to 50 by volume mixture of hexane and ethylene acetate and passed through silica gel and then evaporated to dryness, resulting in the formation of an oil. The structure of the oil residue was conformed as the title compound by infrared spectra and nuclear magnetic resonance; NMR at 0.87 ppm (t, 6H), 1.20–1.48 ppm (m, 18H), 1.70 ppm (m, 4H), and 3.21 ppm (t, 4H).

Similarly by applying the above procedure using the corresponding bromo or chloro starting materials the following compounds can be respectively prepared:

1,1-dicyano-2,2-bis-octylthio-ethylene; 1,1-dicyano-2,2-bis-nonylthioethylene; 1,1-dicyano-2,2-bis-tetradecylthioethylene; 1,1-dicyano-2,2-bis-octadecylthioethylene; and 1,1-dicyano-2,2-bis-(4-dodecylbenzylthio)ethylene.

EXAMPLE 3
1,1-DI(ALLYLTHIO)-2,2-BIS(CARBO-2-ETHYLHEXOXY)ETHYLENE

In this example 272.8 grams (2.25 moles) of allylbromide was added dropwise to a mixture of 1.1 moles of the dipotassium 2,2-bis(carbo-2-ethylhexoxy)-1,1 -dithiolate in 1000 ml of dimethylformamide at 40° C. under a nitrogen atmosphere. The mixture was then heated to 100° C. and stirred vigorously for 48 hours. The mixture was then cooled, filtered. The residue was dissolved in methylene chloride and washed several times with water resulting in a two phase mixture. The organic phase (methylene chloride phase) was dried with anhydrous magnesium sulfate, filtered and then evaporated to dryness affording a translucent reddish-brown oil. The oil was dissolved in hexane, passed through silica gel and then evaporated to dryness affording 335.6 grams of a red-brown oil. The structure of the title compound was conformed by infrared spectra and nuclear molecular resonance analysis; NMR at 0.88 ppm (t, 12H), 1.18–1.45 ppm (m, 16H), 1.62 ppm (m, 2H), 3.20–4.20 ppm (m, 8H), and 5.05–6.01 ppm (m, 6H).

Similarly by applying the above procedure using the appropriate starting materials the following compounds can be respectfully prepared:

1,1-di(3-butenylthio)2,2-bis(carbo-2-ethylhexoxy)ethylene; 1,1-di(4-pentenylthio)2,2-bis(carbo-2-ethylhexoxy)ethylene; 1,1-di(3-methyl-2-butenylthio)2,2-bis(carbo-2-ethylhexoxy)ethylene; 1,1-di(3-phenylallylthio) 2,2-bis(carbo-2-ethylhexoxy)ethylene; and 1,1-di(3-tolylallythio)2,2-bis(carbo-2-ethylhexoxy)ethylene;

EXAMPLE 4
1,1-DI(ETHOXYCARBONYLMETHYLENETHIO)-2,2-BIS(CARBO-2-ETHYLHEXOXY)ETHYLENE

In this example 246.2 grams (2.0 moles) ethyl chloroacetate was added to 1.03 moles of dipotassium 2,2-bis(carbo-2-ethylhexoxy)-1,1-dithiolate in 1000 ml of dimethyl formamide at 100° C. under a nitrogen atmosphere. The mixture was stirred vigorously for 72 hours and then filtered to remove the potassium chloride byproduct. The filtrate was then evaporated to remove the dimethyl formamide solvent and the residue was dissolved in methylene chloride. The methylene chloride solution was washed several times with water, then dried with an anhydrous magnesium sulfate and evaporated to dryness to remove the methylene chloride solvent. The resulting residue was dissolved in hexane, then passed through a silica gel filter with a 15% by volume ethyl acetate-hexane solution. The filtrate was evaporated under vacuum affording 420.1 grams of an oil residue. The structure of the title compound was confirmed by infrared spectra and nuclear magnetic resonance spectra; NMR at 0.88 ppm (t, 12H), 1.10–1.80 ppm (m, 22H), and 3.35–4.40 ppm (m, 12H).

By applying the above procedure using the appropriate starting materials the following compounds can be prepared:

1,1-di(t-butoxycarbornylmethylthio)-2,2-bis(carbo-2-ethylhexoxy)ethylene; 1,1-di(propoxycarbornylmethylthio)-2,2-bis(carbo-2-ethylhexoxy)ethylene; 1,1-di(hexoxycarbornylmethylthio)-2,2-bis(carbo-2-ethylhexoxy)ethylene; 1,1-di(benzyloxycarbornylmethylthio)-2,2-bis(carbo-2-ethylhexoxy)ethylene; and 1,1-di(p-tolyloxycarbornylmethylthio)-2,2-bis(carbo-2-ethylhexoxy)ethylene.

EXAMPLE 5
1,1-BIS(SULFURIZEDPROPYLTHIO)-2,2-BIS(CARBO-2-ETHYLHEXOXY)ETHYLENE

In this example a mixture containing 72.4 grams (4.15 moles) of 1,1 di(allythio)-2,2-bis(2-carbo-2-ethylhexoxy) ethylene and 10.1 grams of powdered sulfur dissolved in 250 ml. of ethylene was heated at reflex (about 136°–144° C.) with stirring for 24 hours. The mixture was then cooled, dissolved in a 95:5 by volume hexane:ethyl acetate mixture and then filtered through silica gel. The filtrate was evaporated to dryness under vacuum affording 81.9 grams of the title compound as a brown oil residue; NMR at 0.85 ppm (t, 12H), 1.30–1.65 ppm (m, 22H), 2.10–3.30 ppm (m, 2H), and 3.85–4.20 ppm (m, 4H).

Similarly by applying the above procedure using the corresponding appropriate unsulfurized olefins starting materials the following compounds can be respectively prepared:

1,1-bis(sulfurizedbutylthio)2,2-bis(carbo-2-ethylhexoxy) ethylene; 1,1-bis(sulfurizedpentylthio)2,2-bis(carbo-2-ethylhexoxy)ethylene; 1,1-bis(sulfurizedisobutyl)2,2-bis (carbo-2-ethylhexoxy)ethylene; 1,1-bis(3-phenyl-sulfurizedpropylthio)2,2-bis(carbo-2-ethylhexoxy)ethylene; and 1,1-bis(3-tolyl-sulfurizedpropylthio)2,2-bis(carbo-2-ethylhexoxy)ethylene.

EXAMPLE 6
1,1-DIBENZYLTHIO-2,2-BIS(CARBO-2-ETHYLHEXOXY)ETHYLENE

A 126.6 g (1.0 mole) of Benzyl chloride was added dropwise to a mixture of 240.4 g (0.5 mole) of Dipottasium 2,2-bis(carbo-2ethylhexoxy)-1,1-dithiolate in 500 ml of Dimethyl formamide at 100° C. under nitrogen atmosphere. The mixture was then heated and stirred vigorously for 72 hours. Upon cooling, the mixture was filtered to remove potassium chloride by product. The filtrate was then evaporated to remove solvent. The remaining dark brown oil was dissolved in hexane and then washed several times with water. The Organic phase was then dried with anhydrous Magnesium sulfate, filtered, and stripped on a Rotovap to yield 249.6 g of a dark red oil. The oil was dissolved in hexane and passed through a short path Silica gel pack on a filter funnel with hexane to remove unreacted Benzyl chloride and then eluted with 25% Ethyl acetate/Hexane solvent. The ethyl acetate/hexane solution was then evaporated to yield 212 g of a dark red oil as the title compound, NMR at 0.81 ppm (t, 12H), 1.2–1.65 ppm (m,18H), 4.10 ppm (m, 4H), 4.60 ppm(s, 4H), and 7.20–7.40 ppm (m, 10H).

EXAMPLE 7
1,1-BIS(2-HYDROXYETHYTHIO)-2,2-BIS(CARBO-2-ETHYLHEXOXY)ETHYLENE

A 712 g (6.10 moles) of 2-bromoethanol was added dropwise to a mixture of 1445 g (3.0 moles) of Dipottasium 2,2-bis(carbo-2-ethylhexoxy)-1,1-dithiolate in 1400 ml of Dimethyl formamide at 100° C. under nitrogen atmosphere. The mixture was then heated and stirred vigorously for 72 hours. Upon cooling, the mixture was filtered to remove potassium chloride by product. The filtrate was then evaporated to remove solvent. The remaining amber brown oil was dissolved in Methylene Chloride and then washed several times with water. The Organic phase was then dried with anhydrous Magnesium sulfate, filtered, and stripped on a Rotovap to yield 1060 g of a brown oil. The oil was dissolved in hexane and passed through a short path Silica gel pack on a filter funnel with 50:50 Ethyl acetate/Hexane solvent. The ethyl acetate/hexane eluent was then evaporated to yield 790 g of a brown oil as the title compound, NMR at 0.84 ppm (t, 12H), 1.2–1.65 ppm (m, 18H), 2.90–3.95 ppm (m, 6H), and 4.10 ppm (m, 4H).

EXAMPLE 8
BORATED 1,1-BIS(2-HYDROXYETHYLTHIO)-2,2-BIS(CARBO-2-ETHYLHEXOXY)ETHYLENE

A mixture (suspension) of 1010 g (2.05 mole) of 1,1-Bis (2-hydroxyethylthio)-2,2-bis(carbo-2-ethylhexoxy)ethylene and 253 g (4.1 moles) of Boric Acid was stirred in 2500 ml of Toluene in a 5 L flask equipped with a Dean Stark Trap and condenser and under Nitrogen Blanket. The mixture was heated to 95° C. and stirred vigorously for 3 hours. The mixture was then heated to reflux (108°–115° C.) and water was collected from the azeotropic fraction (72 ml in 5 hr.). The mixture was then cooled and filtered to remove excess Boric Acid. The filtrate was evaporated to yields 1026 g of a clear gold colored oil as the title compound; NMR at 0.83 ppm (t, 12H), 1.20–1.65 ppm (m, 18H), and 3.10–4.15 ppm (m, 9H).

EXAMPLE 9

In this example the title compounds of Examples 1–8 were respectively formulated into a finished lubricating oil at a concentration of 1% wt. The finished lubricating oil contained small amounts of standards detergents, ashless dispersants, foam inhibition etc. to simulate a commercial finish lubricating oil including two wear inhibiting materials i.e. a borated dispersant and commercial zinc dithiophosphate. Thus, the finished lubricating oil used as the control in this test possessed wear protection and extreme pressure properties significantly superior to base oil.

The respective formulations were tested for extreme pressure wear inhibition by ASTM tests ASTM D2782 and ASTM D2783 and compared with the identical lubricating oil but without the compounds of the present invention. The test results thus show whether the tested compounds can be used with zinc dithiophosphate to provide wear protection beyond that provided by zinc dithiophosphate and correspondingly reflect whether the compound can be used to reduce the amount of zinc dithiophosphate in conventional lubricating oil compositions such as for example, used spark and diesel engine crank cases. The results for the ASTM D2782 test and ASTM D2783 test are reported in Tables 1 and 2, respectively, hereinbelow. Both tests involve a weight loading mechanism thus the higher the load, indicated by the number reported in the Tables, the better the wear protection. The Timken test (ASTM D2782) reports two load values; a satisfactory or OK load weight and a score load weight which is the minimum weight at which wear metal scoring or seizure occurs. An increase in either value is considered indicative of improved wear protection. For the ASTM D2783 test the lead-wear index weight is reported in Table 2.

TABLE 1

Timken Method - ASTM D2782

| Test Compound Example No. | Concentration of Test Compound (wt. %) | Concentration of Zn DTP | OK Value lbs | Score Value lbs |
|---|---|---|---|---|
| 1 | 1% | 0.69% | 20 | 25 |
| 2 | 1% | 0.69% | 10 | 15 |
| 3 | 1% | 0.69% | 15 | 20 |
| 4 | 1% | 0.69% | 15 | 20 |
| 5 | 1% | 0.69% | 20 | 25 |
| 6 | 1% | 0.69% | 15 | 20 |
| 7 | 1% | 0.69% | 20 | 25 |
| 8 | 1% | 0.69% | 20 | 25 |
| Control | 0 | 1.38% | 10 | 15 |

TABLE 2

ASTM D2783

| Test Compound Example No. | Concentration of Test Compound (wt. %) | Concentration of Zn DTP | Load Wear Index kg |
|---|---|---|---|
| 1 | 1% | 0.69% | 35.62 |
| 2 | 1% | 0.69% | 41.90 |
| 3 | 1% | 0.69% | 30.58 |
| 4 | 1% | 0.69% | 34.28 |
| 5 | 1% | 0.69% | 35.32 |
| 6 | 1% | 0.69% | 37.70 |
| 7 | 1% | 0.69% | 35.80 |
| 8 | 1% | 0.69% | 30.85 |
| Control | 0 | 1.38% | 29.80 |

All of the test compounds of the invention exhibited substantially superior wear protection performance in at least one of the tests and Compound 2 while only exhibiting equivalent performance in the Timken test was clearly superior to the control and all of the other test compounds in the ASTM D2783 test.

While the present invention has been described with reference to specific embodiments, this application is intended to cover those various changes and substitutions that may be made by those skilled in the art without departing from the spirit and scope of the appended claims.

What is claimed is:

1. A compound having the formula

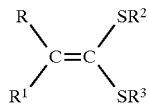

wherein R and $R^1$ are independently:
   (a) alkoxycarbonyl having four through thirty carbon atoms,
   (b) aryloxycarbonyl having seven through thirty carbon atoms,
   (c) alkenyloxycarbonyl having eight through thirty carbon atoms,
   (d) alkylcarbonyl having four through thirty carbon atoms,
   (e) arylcarbonyl having seven through thirty carbon atoms,
   (f) alkenylcarbonyl having eight through thirty carbon atoms,
   (g) alkylsulfonyl having four through thirty carbon atoms,
   (h) arylsulfonyl having seven through thirty carbon atoms,
   (i) alkenylsulfonyl having eight through thirty carbon atoms,
   (j) substituted aminocarbonyl having one through thirty carbon atoms,
   (k) alkylphosphoryl having four through thirty carbon atoms,
   (l) arylphosphoryl having seven through thirty carbon atoms,
   (m) alkenylphosphoryl having eight through thirty carbon atoms, or
   (n) aryl having one through thirty carbon atoms,
or R and $R^1$ together with the carbon atom to which they are joined form:
   (o) a saturated or unsaturated carbocycle having five or six carbon atoms optionally substituted with one or two alkyl groups independently having one through thirty carbon atoms,
$R^2$ and $R^3$ are independently:
   (p) alkyl having seven through thirty carbon atoms,
   (q) hydroxyalkyl having two through twenty carbon atoms,
   (r) alkenyl having three through thirty carbon atoms,
   (s) sulfurized alkyl having three through thirty carbon atoms and one or two sulfur atoms,
   (t) alkoxycarbonylalkyl wherein the alkoxy moiety has two through five carbon atoms and the alkyl moiety has one through ten carbon atoms;
   (u) arylalkyl having seven through thirty carbon atoms, or
   (v) borated hydroxyalkyl having three through thirty carbon atoms,
with the proviso that R, $R^1$, $R^2$ and $R^3$ together contain sufficient carbon atoms to render the compound oil soluble in an oil of lubricating viscosity.

2. The compound of claim 1 wherein R and $R^1$ are independently alkoxycarbonyl having four through thirty carbon atoms or R and $R^1$ together with the carbon atom to which they are joined form a saturated or unsaturated carbocycle having five or six carbon atoms optionally substituted with one or two alkyl groups independently having one through thirty carbon atoms.

3. The compound of claim 2 wherein the R substituent is identical to the $R^1$ substituent.

4. The compound of claim 2 wherein the $R^2$ substituent is identical to the $R^3$ substituent.

5. The compound of claim 4 wherein the R substituent is identical to the $R^1$ substituent.

6. The compound of claim 2 wherein the R and $R^1$ are independently alkoxycarbonyl having eight to thirty carbon atoms.

7. The compound of claim 6 wherein the R and $R^1$ are each alkoxycarbonyl.

8. The compound of claim 7 wherein R and $R^1$ are each carbo-2-ethylhexoxy.

9. The compound of claim 2 wherein the $R^2$ and $R^3$ are both arylalkyl having seven through thirty carbon atoms.

10. A lubricating oil composition comprising a major amount of an oil of lubricating viscosity and amount of a compound or mixture of compounds having the formula:

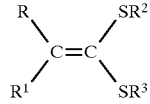

(a) wherein R and $R^1$ are independently cyano, alkoxycarbonyl having four through thirty carbon atoms or R and $R^1$ together with the carbon atom to which they are joined form a saturated or unsaturated carbocycle having five or six carbon atoms optionally substituted with one or two alkyl groups independently having one through thirty carbon atoms, and
   (b) $R^2$ and $R^3$ are independently alkyl having seven through thirty carbon atoms, hydroxyalkyl having two through twenty carbon atoms, alkenyl having three through thirty carbon atoms, sulfurized alkyl having three through thirty carbon atoms and one or two sulfur atoms, alkoxycarbonylalkyl wherein the alkoxy moiety has two through five carbon atoms and the alkyl moiety has one through ten carbon atoms, arylalkyl having seven through thirty carbon atoms, or borated hydroxyalkyl having three through thirty carbon atoms,
with the proviso that R, $R^1$, $R^2$ and $R^3$ together contain sufficient carbon atoms to render the compound oil soluble in an oil of lubricating viscosity, wherein said amount of compound or mixture of compounds is effective to improve extreme pressure or antiwear properties.

11. A lubricating oil composition according to claim 10 wherein the $R^2$ substituent is identical to the $R^3$.

12. A lubricating oil composition according to claim 10 wherein the R and $R^1$ are each carbo-2-ethylhexoxy.

13. A method for providing wear protection for sliding metal parts which comprises lubricating said parts with the lubricating composition of claim 10.

14. A concentrate comprising about 5 to 95 wt. % of a compatible organic liquid diluent and about from 5 to 95 wt. % of a compound or mixture of compounds having the formula:

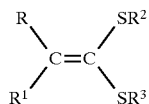

(I)

(a) wherein R and $R^1$ are independently cyano, alkoxycarbonyl having four through thirty carbon atoms or R and $R^1$ together with the carbon atom to which they are joined form a saturated or unsaturated carbocycle having five or six carbon atoms optionally substituted with one or two alkyl groups independently having one through thirty carbon atoms, and (b) $R^2$ and $R^3$ are independently alkyl having seven through thirty carbon atoms, hydroxyalkyl having two through twenty carbon atoms, alkenyl having three through thirty carbon atoms, sulfurized alkyl having three through thirty carbon atoms and one or two sulfur atoms, alkoxycarbonylalkyl wherein the alkoxy moiety has two through five carbon atoms and the alkyl moiety has one through ten carbon atoms, arylalkyl having seven through thirty carbon atoms, or borated hydroxyalkyl having three through thirty carbon atoms, with the proviso that R, $R^1$, $R^2$ and $R^3$ together contain sufficient carbon atoms to render the compound oil soluble in an oil of lubricating viscosity.

15. A lubricating grease composition comprising an oil of lubricating viscosity, about from 5 to 95 wt. % of a compatible thickening agent and an amount of a compound or mixture of compounds having the formula:

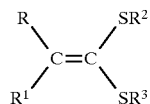

(I)

(a) wherein R and $R^1$ are independently cyano, alkoxycarbonyl having four through thirty carbon atoms or R and $R^1$ together with the carbon atom to which they are joined form a saturated or unsaturated carbocycle having five or six carbon atoms optionally substituted with one or two alkyl groups independently having one through thirty carbon atoms, and (b) $R^2$ and $R^3$ are independently alkyl having seven through thirty carbon atoms, hydroxyalkyl having two through twenty carbon atoms, alkenyl having three through thirty carbon atoms, sulfurized alkyl having three through thirty carbon atoms and one or two sulfur atoms, alkoxycarbonylalkyl wherein the alkoxy moiety has two through five carbon atoms and the alkyl moiety has one through ten carbon atoms, arylalkyl having seven through thirty carbon atoms, or borated hydroxyalkyl having three through thirty carbon atoms, with the proviso that R, $R^1$, $R^2$ and $R^3$ together contain sufficient carbon atoms to render the compound oil soluble in an oil of lubricating viscosity, wherein said amount of said compound or mixture of compound is effective to improve wear protection or extreme pressure properties.

* * * * *